United States Patent
Treybig et al.

(10) Patent No.: US 6,964,940 B1
(45) Date of Patent: Nov. 15, 2005

(54) METHOD OF PREPARING QUATERNIZED AMIDOAMINE SURFACTANTS

(75) Inventors: Duane S. Treybig, Sugar Land, TX (US); Grahame N. Taylor, Houston, TX (US); James A. Krogh, Janesville, WI (US); Michael J. Williams, Madison, WI (US)

(73) Assignees: Nalco Energy Services, L.P., Sugar Land, TX (US); Tomah Products, Inc., Milton, WI (US)

( * ) Notice: Subject to any disclaimer, the term of this patent is extended or adjusted under 35 U.S.C. 154(b) by 221 days.

(21) Appl. No.: 10/338,442

(22) Filed: Jan. 8, 2003

(51) Int. Cl.$^7$ .................. C09K 7/02; C07C 211/62; B01F 17/18
(52) U.S. Cl. .................. 507/129; 507/281; 507/291; 516/20; 516/67; 516/69; 516/102; 516/203; 564/281; 564/291
(58) Field of Search .................. 516/67, 69, 20, 516/102, 203; 564/281, 291; 507/129, 239, 507/240

(56) References Cited

U.S. PATENT DOCUMENTS

| | | | | |
|---|---|---|---|---|
| 3,287,305 A | * | 11/1966 | Maeder | 523/410 |
| 3,301,812 A | * | 1/1967 | Ferrigno | 521/57 |
| 4,851,138 A | * | 7/1989 | Jaroschek et al. | 510/330 |
| 6,258,859 B1 | | 7/2001 | Dahayanake et al. | |
| 2004/0214725 A1 | * | 10/2004 | Moss | 507/129 |

FOREIGN PATENT DOCUMENTS

| | | |
|---|---|---|
| EP | 0 327 379 A2 | 8/1989 |
| WO | WO 01/18147 A1 | 3/2001 |

* cited by examiner

*Primary Examiner*—Jeffrey B. Robertson
(74) *Attorney, Agent, or Firm*—Michael B. Martin; Thomas M. Breininger

(57) ABSTRACT

This invention is a method of preparing a quaternized amidoamine surfactant comprising reacting an amidotertiaryamine of formula with methyl halide and alkylene oxide, an aqueous quaternized amidoamine surfactant composition, a gelled aqueous composition comprising the quaternized amidoamine surfactant composition and one or more salts or alcohols and use of the gelled aqueous composition for fracturing subterranean formations.

24 Claims, No Drawings

METHOD OF PREPARING QUATERNIZED AMIDOAMINE SURFACTANTS

TECHNICAL FIELD

This invention is a method of preparing a quaternized amidoamine surfactant, easily handled compositions comprising the quaternized amidoamine surfactant, a gelled aqueous composition comprising the quaternized amidoamine surfactant and use of the gelled aqueous composition to fracture a subterranean formation.

BACKGROUND OF THE INVENTION

Gelled aqueous compositions comprising quaternized amidoamine surfactants are disclosed in WO 01/18147. The quaternized amidoamine surfactant is prepared by quaternizing an alkylamidopropyldimethylamine with one or more halides such as methyl chloride, ethyl chloride, benzyl chloride, vinyl chloride, butyl chloride, methyl sulfate, chlorohydroxyalkylsulfonate, chloroalkylsulfonates, and the like.

In certain instances, use of the halides disclosed in WO 01/18147 results in incomplete quaternization of the alkylamidopropyltrimethylamine, providing a mixture of quaternized and unquaternized amine. As only the quaternized amine is suitable for preparing the gelled aqueous composition, the unquaternized material must be either separated, or alternatively, used as a mixture with the quaternized amine, resulting in a less effective gelling agent.

Accordingly, there is an ongoing need to develop improved methods of preparing quaternized amidoamine surfactants.

SUMMARY OF THE INVENTION

We have discovered that complete quaternization can be readily accomplished by reacting the tertiary amine with methyl halide followed by an alkylene oxide such as ethylene oxide or propylene oxide.

Accordingly, this invention is a method of preparing a quaternized amidoamine surfactant of formula

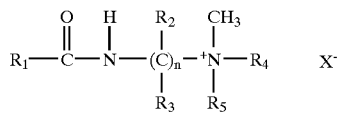

wherein
  $R_1$ is selected from the group consisting of $C_{12}$–$C_{30}$ alkyl, $C_{12}$–$C_{30}$ alkenyl, $C_{12}$–$C_{30}$ arylalkyl and $C_{12}$–$C_{30}$ cycloalkylalkyl,
  $R_2$ and $R_3$ are independently selected at each occurrence from hydrogen or $C_1$–$C_4$ alkyl,
  $R_4$ and $R_5$ are independently selected from $C_1$–$C_4$ alkyl, $C_1$–$C_4$ alkoxyalkyl and $C_1$–$C_4$ hydroxyalkyl,
  X is halide; and
  n is an integer from 1 to about 10 comprising reacting an amidotertiaryamine of formula

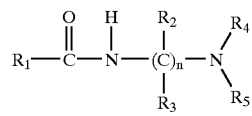

with methyl halide and alkylene oxide.

DETAILED DESCRIPTION OF THE INVENTION

Definitions of Terms

"Alcohol" means a straight or branched aliphatic hydrocarbon substituted by one hydroxy group. Representative alcohols include methanol, ethanol, propanol, isopropanol, butanol, 2-ethylhexanol, hexanol, octanol, decanol, and the like.

"Alkenyl" means a monovalent group derived from a straight or branched hydrocarbon containing at least one carbon—carbon double bond by the removal of a single hydrogen atom.

"Alkoxy" means a $C_1$–$C_4$ alkyl group attached to the parent molecular moiety through an oxygen atom. Representative alkoxy groups include methoxy, ethoxy, propoxy, butoxy, and the like. Methoxy and ethoxy are preferred.

"Alkyl" means a monovalent group derived from a straight or branched chain saturated hydrocarbon by the removal of a single hydrogen atom. Representative alkyl groups include methyl, ethyl, n- and iso-propyl, n-, sec-, iso- and tert-butyl, and the like.

"Alkylene" means a divalent group derived from a straight or branched chain saturated hydrocarbon by the removal of two hydrogen atoms, for example methylene, 1,2-ethylene, 1,1-ethylene, 1,3-propylene, 2,2-dimethylpropylene, and the like.

"Alkylene oxide" means an aliphatic $C_2$ to $C_4$ epoxide, for example ethylene oxide, propylene oxide and butylene oxide.

"Aryl" means substituted and unsubstituted aromatic carbocyclic radicals and substituted and unsubstituted heterocyclic radicals having about 5 to about 14 ring atoms. Representative aryl include phenyl naphthyl, phenanthryl, anthracyl, pyridyl, furyl, pyrrolyl, quinolyl, thienyl, thiazolyl, pyrimidyl, indolyl, and the like. The aryl is optionally substituted with one or more groups selected from hydroxy, halogen, $C_1$–$C_4$ alkyl and $C_1$–$C_4$ alkoxy.

"Arylalkyl" means an aryl group attached to the parent molecular moiety through an alkylene group. The number of carbon atoms in the alkylene group is selected such that there is a total of about 12 to about 30 carbon atoms in the arylalkyl group.

"Cycloalkyl" means a monovalent group derived from a monocyclic or bicyclic saturated carbocyclic ring compound by the removal of a single hydrogen atom. Representative cycloalkyl include cyclopropyl, cyclobutyl, cyclopentyl, cyclohexyl, bicyclo[2.2.1]heptanyl, bicyclo[2.2.2]octanyl, and the like.

"Cycloalkylalkyl" means a cycloalkyl group attached to the parent molecular moiety through an alkylene group. The number of carbon atoms in the alkylene group is selected such that there is a total of about 12 to about 30 carbon atoms in the cycloalkylalkyl group.

"Diol" means a straight or branched aliphatic hydrocarbon substituted by two hydroxy groups. Representative diols include ethylene glycol, 1,2-propylene glycol, butylene glycol, hexylene glycol, and the like.

"Halo" and "halogen" mean chlorine, fluorine, bromine and iodine.

"Hydroxyalkyl" means a $C_1$–$C_4$ alkyl substituted by one to three hydroxyl groups with the proviso that no more than one hydroxy group may be attached to a single carbon atom of the alkyl group. Representative hydroxyalkyl include hydroxyethyl, 2-hydroxypropyl, and the like.

"Salt" means the alkali or alkaline earth metal or ammonium salt of an inorganic or organic anionic counterion. Representative alkali or alkaline earth metals include sodium, lithium, potassium, calcium, magnesium, and the like. Representative anionic counterions include chloride, bromide, iodide, salicylate, toluenesulfonate, 3-hydroxy-2-naphthalenecarboxylate, cumene sulphonate, p- and m-chlorobenzoates, t-butyl and ethyl phenate, 2,5-dichlorophenate, 2,4,5-trichlorophenate, 2,3,5,6-tetrachlorophenate, p-methylphenate, m-chlorophenate, 3,5,6-trichloropicolinate, 4-amino-3,5,6-trichloropicolinate, 2,4-dichlorophenoxyacetate and the like.

PREFERRED EMBODIMENTS

This invention is a method of preparing a quaternized amidoamine surfactant comprising reacting a tertiaryamidoamine of formula

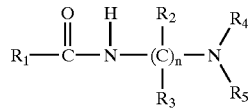

where $R_1$–$R_5$ and n are as defined herein with methyl halide and alkylene oxide.

The tertiary amidoamine is preferably dissolved in a $C_1$–$C_4$ alcohol and reacted with about 1 to about 1.5 molar equivalents of a methyl halide, preferably about 1.1 to about 1.3 molar equivalents of methyl chloride, at a temperature of about 30° C. to about 100° C. for about 6 to about 27 hours and then with about 0.02 to about 0.11 molar equivalents of ethylene oxide for about 3 to about 16 hours to form the quaternized amidoamine.

Optionally, additional methyl halide (about 0.02 to about 0.1 molar equivalents) is added after addition of the ethylene oxide to quaternize any remaining unreacted tertiary amine.

Isopropanol and methanol are the preferred solvents for the quaternization as they exhibit the best ability at solubilizing the quaternary salt by breaking the gel phase formed. Isopropanol is preferred over methanol because of the toxicity issues associated with use of methanol.

After the quaternized amidoamine in alcohol is prepared, it may be necessary to dilute it with more alcohol, a diol and water if the product is a solid or not very pourable at room temperature. Isopropanol is the preferred alcohol and 1,2-propyleneglycol is the preferred diol for dilution. Surprisingly, water drops the pour point.

The amidotertiaryamine is prepared by condensing a N,N-dialkyl alkylenediamine of formula

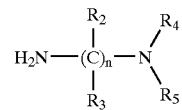

wherein $R_2$–$R_5$ and n are defined herein with an acyl halide, ester or carboxylic acid of formula

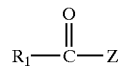

wherein $R_1$ is defined herein and Z is H, halogen or alkoxy.

Typically, the N,N-dialkyldiamine 2 is reacted with about 1.0 to about 11.1 molar equivalents of the fatty carboxylic acid, ester or acid choride without a solvent at a temperature of about 60° C. to about 140° C. until water evolution ceases, typically about 8 to about 30 hours.

Representative N,N-dialkyldiamines include 3-(dimethylamino)propylamine; 3-(diethylamino)propylamine; N,N,N',N'-tetramethyl-1,3-propanediamine; N,N-dimethylethylenediamine; N,N-diethylethylenediamine; N,N-dimethylbutanediamine; N,N-dimethyl-1,6-hexanediamine; N,N-bis(2-hydroxyethyl)ethylenediamine; N,N,N'-trimethylethylenediamine; N,N,N'-trimethyl-1,3-propanediamine; N,N-dimethyl-N'-ethylethylenediamine; and N,N,N'-triethylethylenediamine.

The carboxylic acids, esters or acid chlorides 1 may be saturated and unsaturated and contain between 12 to 30 carbons exclusive of the alkoxy group of the ester. Alkyl and alkenyl groups may be straight chain or branched.

Representative unsaturated carboxylic acids $RCO_2H$ include 6-octadecenoic acid (oleic acid, $C_{18}$); 9,11,13-octadecatrienoic acid ($C_{18}$); 12-hydroxy-9-octadecenoic acid ($C_{18}$); 5,8,11,14-eicosatetraenoic acid ($C_{20}$); eicosenoic acid ($C_{20}$); heneicosenoic acid ($C_{21}$); 13-docosenoic acid (erucic acid, $C_{22}$); tetracosenoic acid ($C_{24}$); pentacosenoic acid ($C_{25}$), heptacosenoic acid ($C_{27}$); and the like and mixtures thereof.

Representative saturated carboxylic acids $RCO_2H$ include eicosanoic acid ($C_{20}$); heneicosanoic acid ($C_{21}$); docosenoic acid (behenic acid, $C_{22}$); tricosanoic acid ($C_{23}$); tetracosanoic acid ($C_{24}$); pentacosanoic acid ($C_{25}$); heptacosanoic acid ($C_{27}$); and the like and mixtures thereof.

Representative branched unsaturated and saturated acids $RCO_2H$ include 3-methylhexadecanoic acid; 7-methylhexadecanoic acid; 13-methylhexadecanoic acid; 14-methyl-11-eicosenoic acid; 2-hydroxy-18-oxa-19-methyl-4-eicosenoic acid; and the like and mixtures thereof.

Representative alkyl esters of saturated and unsaturated acids $RCO_2R'$ include 2-methylhexadecanoic acid methyl ester; 8-ethyl-9-methylhexadecanoic acid methyl ester; 18-methyl-15-eicosenoic acid methyl ester; 14-methyl-11-eicosenoic acid methyl ester; 9,12,15-octadecatrienoic acid methyl ester; docosanoic acid methyl ester; high erucic rape seed oil, canola oil, triglyceride esters of oleic acid, and the like and mixtures thereof.

Acid chlorides of saturated and unsaturated acids RCOCl include include oleoyl chloride, octadecanoyl chloride, docosanoyl chloride, eicosanoyl chloride, 9-tetracosenoyl chloride, 15-tetracosenoyl chloride, and the like and mixtures thereof.

In a preferred aspect of this invention, $R_1$ is selected from the group consisting of $C_{12}$–$C_{30}$ alkyl and $C_{12}$–$C_{30}$ alkenyl.

Quaternary amidoamine surfactants that contain a carbon—carbon double bond typically have lower melting points than the saturated counterpart. In some cases, this lower melting point allows for preparation of a composition that is liquid at room temperature.

Accordingly, in another preferred aspect of this invention, $R_1$ is $C_{12}$–$C_{30}$ alkenyl.

In another preferred aspect, $R_1$ is $C_{18}$–$C_{30}$ alkenyl.

In another preferred aspect, $R_1$ is $C_{18}$–$C_{30}$ alkenyl; $R_2$ and $R_3$ are hydrogen; $R_4$ and $R_5$ are $C_1$–$C_4$ alkyl or $C_1$–$C_4$ hydroxyalkyl; n is an integer of 2 to about 6 and X is Cl.

The unsaturated amidoamine quaternary surfactants are liquids at 60 weight percent or higher solids when formulated with solvents such as isopropanol, methanol, polyethylene glycols, 1,2-propanediol and water. This permits application of the composition in the field at a high activity in most parts of the world as a liquid.

Accordingly, in another aspect, this invention is a pourable aqueous composition comprising
a) about 75 to about 90 weight percent of the quaternized amidoamine surfactant solution in alcohol described herein;
b) about 1 to about 15 weight percent of one or more $C_2$–$C_6$ diols; and
c) about 1 to about 10 weight percent water.

In another preferred aspect, the $C_2$–$C_6$ diol is 1,2-propylene diol.

The solution of quaternized amidoamine surfactant in water/alcohol in combination with one or more organic or inorganic salts or one or more $C_6$–$C_{10}$ alcohols is used to viscosify water or brine to form a gelled aqueous composition for carrying proppants into subterranean formations during hydraulic fracturing of the formation. The gelled aqueous composition may also be used in detergent and cosmetic formulations and as a drift control agent in agricultural formulations.

Accordingly, in another preferred aspect, this invention is a gelled aqueous composition comprising
a) about 0.5 to about 10 weight percent of the quaternized amidoamine surfactant in water/alcohol/diol described herein;
b) about 0.5 to about 10 weight percent of one or more salts or one or more $C_6$–$C_{10}$ alcohols; and
c) water.

The gelled aqueous solution is preferably prepared by adding the solution of quaternized amidoamine surfactant in water/alcohol/diol to water and mixing or agitating. Then the salt, an aqueous solution of the salt or $C_6$–$C_{10}$ alcohol is added to the surfactant/water/alcohol/diol solution in water and the solution is mixed or agitated.

Salts of ammonia and monovalent cations such as sodium and potassium are preferred. Preferred inorganic salts include ammonium chloride, potassium chloride and mixtures thereof. A preferred organic salt is sodium salicylate. Both organic and inorganic salts can be used in the same formulation.

In general, a higher viscosity formulation is obtained when the hydrophobic portion of the quaternized surfactant amidoamine consists of more than 15 carbons, preferably more than 18 carbons and more preferably at least 22 carbons up to about 30 carbons. Hydrophobic portion means the portion of the surfactant that contains only carbon atoms and no heteroatoms.

The gelled aqueous composition of this invention is particularly useful for carrying proppant into subterranean formations during hydraulic fracturing of the formation.

In hydraulic fracturing of subterranean formations, a fracturing fluid is injected through a wellbore penetrating the formation and is forced against the formation by pressure, forcing the formation strata or rock to crack and fracture. A particulate proppant is then placed in the fracture to prop open the fracture and provide improved flow of oil, gas or water into the wellbore.

Accordingly, in a preferred aspect, the viscoelastic surfactant composition of this invention further contains a proppant.

Suitable particulate proppant materials are insoluble in the fluids contained in the subterranean formation and include sand, bauxite, walnut shells, glass beads, polystyrene beads and the like.

In general, the gelled aqueous composition comprises about 0.5 to about 8 pounds per gallon of the proppant, but in certain instances may contain up to 22 pounds or more.

The fracturing fluid may contain other components conventional in the art including gasses such as air, nitrogen or carbon dioxide to provide an energized fluid or a foam. Other conventional ingredients such as corrosion inhibitors, fluid-loss additives, and the like may also be included.

Other commonly used fracturing fluids are based on polysaccharides, such as guar. A disadvantage of the polysaccharide viscosifiers is that they contain materials that concentrate in the formation during the course of the hydraulic fracturing treatment, damaging the formation (reducing the porosity) and reducing the production of hydrocarbons after the fracturing event.

Quaternized amidoamine surfactants form micelles that are able to viscosify the fluid and carry the proppant into the fractured rock. As oil is produced it breaks the micelle, allowing the components to be removed. Therefore, a breaker material may not be necessary, thereby reducing cost and improving clean-up of the fluid from the formation.

The foregoing may be better understood by reference to the following Examples, which are presented for purposes of illustration and are not intended to limit the scope of this invention.

EXAMPLE 1

Preparation of 3-erucylamidopropyl(dimethyl)amine

The title compound is prepared by heating a mixture of erucic acid (416 g, 1.242 moles, Iodine value=74–78) and 3-(dimethylamino)propylamine (126.9 g, 1.242 moles) in a 2 liter high pressure vessel at a temperature between 50 and 150° C. for 24 hours to give the title compound.

EXAMPLE 2

Preparation of 3-erucylamidopropyltrimethyl ammonium chloride

A mixture of 3-erucylamidopropyl(dimethyl)amine (463.7 g), prepared as in Example 1, methyl chloride (60 g, 1.19 moles) and isopropanol (152 grams) are reacted in a 2 liter pressure vessel at a temperature between 30° C. and 100° C. for 24 hours. Ethylene oxide (18 g) is then added to the reaction mixture. After 6 hours, the pressure stabilizes and an additional 6 g (0.12 moles) of methyl chloride are added to quaternize the remaining amine. A chloride titration of the product indicates that the material is 69.53% active. The product is a transparent colored liquid at room temperature.

EXAMPLE 3

Preparation of an aqueous 3.98 weight percent 3-erucylamidopropyltrimethyl ammonium chloride, 1.74 weight percent isopropanol, 2.0 weight percent KCl solution 3-Erucylamidopropyltrimethyl ammonium chloride (6.3 g of a 69.53 weight percent solution in isopropanol), prepared as in Example 2 is blended with water (90.4 g). Potassium chloride (2.2 g) is added and the contents are blended. Additional water (11.1 g) is added and contents are blended to give the title composition as a viscous solution.

EXAMPLE 4

Preparation of an aqueous 3.98 weight percent 3-erucylamidopropyltrimethyl ammonium chloride, 1.74 weight percent isopropanol, 4.0 weight percent KCl solution.

3-Erucylamidopropyltrimethyl ammonium chloride (6.3 g of a 69.53 weight percent solution in isopropanol), prepared as in Example 2, is blended with water (92 g). Potassium chloride (4.4 g) is added and the contents are blended. Additional water (7.4 g) is added and contents are blended to give the title composition as a viscous solution.

EXAMPLE 5

Preparation of an aqueous 4.02 weight percent bis(2-hydroxyethyl)-13-docosen-1-amine methyl chloride quaternary salt, 1.34 weight percent isopropanol, 4.0 weight percent KCl solution.

Bis(2-hydroxyethyl)-13-docosen-1-amine methyl chloride quaternary salt (5.9 g of a 75 weight percent solution in isopropanol, available from Akzo Nobel as Ethoquad E/12–75), is blended with water (91.3 g). Potassium chloride (4.4 g) is added and the contents are mixed. Additional water (7.4 g) is added and contents are mixed to give the title composition as a viscous solution.

EXAMPLE 6

The viscosity of the compositions of Examples 3, 4 and 5 is measure between 81° F. and 275° F. with a Fann 50 Rheometer equipped with a R1-B5 spindle setting at a shear rate of 118 rpm. The results are shown in Table 1. A viscosity of 100 cps at a shear rate of 100 sec$^{-1}$ (118 rpm) is preferred to fracture the formation and carry proppant.

TABLE 1

Viscosity of Representative KCl Salt Compositions

| Example 3 2 wt. % KCl | | Example 4 4 wt. % KCl | | Example 5 4 wt. % KCl | |
| --- | --- | --- | --- | --- | --- |
| Temperature (° F.) | Viscosity (cps) | Temperature (° F.) | Viscosity (cps) | Temperature (° F.) | Viscosity (cps) |
| 256 | 32 | 240 | 20 | 242 | 23 |
| 249 | 30 | 230 | 72 | 233 | 27 |
| 239 | 25 | 219 | 157 | 226 | 30 |
| 229 | 29 | 211 | 172 | 219 | 38 |
| 218 | 31 | 202 | 162 | 209 | 59 |
| 212 | 31 | 194 | 154 | 202 | 91 |
| 203 | 32 | 184 | 154 | 193 | 156 |
| 194 | 63 | 175 | 169 | 183 | 262 |
| 184 | 99 | 166 | 180 | 174 | 341 |
| 175 | 134 | 156 | 173 | 165 | 376 |
| 166 | 151 | 146 | 168 | 157 | 401 |
| 156 | 146 | 136 | 179 | 147 | 505 |
| 147 | 121 | 127 | 214 | 138 | 615 |
| 138 | 112 | 119 | 237 | 128 | 691 |
| 130 | 122 | 110 | 238 | 116 | 721 |
| 120 | 137 | 101 | 236 | 103 | 636 |
| 111 | 157 | 93 | 220 | 90 | 606 |
| 103 | 162 | 87 | 232 | 81 | 602 |
| 96 | 173 | 84 | 717 | | |
| 91 | 197 | | | | |
| 87 | 339 | | | | |

As shown in Table 1, the composition of Example 4 provides more than 100 cps of viscosity at 219° F. while the composition of Example 5 provides more than 100 cps of viscosity at 193° F. Therefore, the composition of Example 4 can be used to fracture hotter wells than that of Example 5.

EXAMPLE 7

Preparation of an aqueous 3.98 weight percent 3-erucylamidopropyltrimethyl ammonium chloride, 1.75 weight percent isopropanol, 4.1 weight percent NH$_4$Cl solution 3-Erucylamidopropyltriimethyl)ammonium chloride (6.3 g of a 69.53 weight percent solution in isopropanol), prepared as in Example 2, is blended with water (89.4 g). Ammonium chloride (4.5 g) is added and the contents blended. Additional water (10.0 g) is added and contents are blended to give the title composition as a viscous solution.

EXAMPLE 8

Preparation of an aqueous 3.98 Weight Percent 3-erucylamidopropyltrimethyl ammonium chloride, 1.75 weight percent isopropanol, 5.1 weight percent NH$_4$Cl solution 3-Erucylamidopropyltrimethylammonium chloride (6.3 g of a 69.53 weight percent solution in isopropanol), prepared as in Example 2, is blended with water (87.3 g). Ammonium chloride (5.6 g) is added and the contents are blended. Additional water (10.9 g) is added and the contents are blended to give the title composition as a viscous liquid.

EXAMPLE 9

The viscosity of the compositions of Examples 7 and 8 is determined between 85° F. and 275° F. with a Fann 50

Rheometer equipped with a R1-B5 spindle setting at a shear rate of 118 rpm. The results are shown in Table 2. A viscosity of 100 cps at a shear rate of 100 sec$^{-1}$ is preferred to fracture the formation and carry proppant.

TABLE 2

Viscosity of Representative NH$_4$Cl Salt Compositions

| Temperature (° F.) | Example 7 4.1 wt. % NH$_4$Cl Viscosity (cps) | Temperature (° F.) | Example 8 5.1 wt. % NH$_4$Cl Viscosity (cps) |
|---|---|---|---|
| 278 | 9 | 285 | 8 |
| 277 | 10 | 284 | 10 |
| 276 | 10 | 282 | 11 |
| 274 | 10 | 280 | 13 |
| 272 | 11 | 277 | 17 |
| 270 | 11 | 273 | 22 |
| 267 | 14 | 265 | 43 |
| 264 | 17 | 257 | 78 |
| 257 | 29 | 249 | 131 |
| 248 | 61 | 242 | 194 |
| 241 | 118 | 234 | 247 |
| 235 | 175 | 227 | 269 |
| 227 | 230 | 219 | 268 |
| 223 | 239 | 209 | 255 |
| 216 | 238 | 204 | 243 |
| 207 | 234 | 197 | 223 |
| 198 | 229 | 188 | 192 |
| 188 | 220 | 180 | 172 |
| 179 | 207 | 171 | 155 |
| 171 | 191 | 162 | 143 |
| 163 | 174 | 153 | 139 |
| 155 | 162 | 143 | 140 |
| 147 | 186 | 134 | 170 |
| 138 | 147 | 127 | 107 |
| 131 | 130 | 118 | 142 |
| 123 | 141 | 110 | 170 |
| 114 | 182 | 102 | 212 |
| 103 | 239 | 94 | 259 |
| 89 | 255 | 89 | 278 |
| 78 | 243 | 85 | 752 |
| 74 | 247 | | |
| 73 | 530 | | |

As shown in Table 2, the compositions of Examples 7 and 8 provide more than 100 cps of viscosity at 241° and 249° F., respectively, while the composition of Example 5 provides more than 100 cps of viscosity at 193° F. Therefore, the compositions of Examples 7 and 8 can be used to fracture hotter wells than the composition of Example 5.

EXAMPLE 10

Preparation of an aqueous 3.98 weight percent 3-erucylamidopropyltrimethyl ammonium chloride, 1.74 weight percent isopropanol, 0.91 weight percent 1,2-propanediol, 0.623 weight percent sodium salicylic acid solution 3-Erucylamidopropyltrimethyl ammonium chloride (6.3 g of a 69.53 weight percent solution in isopropanol), prepared as in Example 2, is blended with 1,2-propanediol (1.0 g). The resulting product is then blended with water (94.1 g). Sodium salt of salicylic acid (2.3 g, 30 weight percent aqueous solution) is added and the contents are blended. Additional water (6.4 g) is added and the contents are blended to give the title composition as a viscous solution.

EXAMPLE 11

Preparation of an aqueous 7.01 weight percent 3-erucylamidopropyltrimethyl ammonium chloride, 3.07 weight percent isopropanol, 1.73 weight percent 1,2-propanediol, 1.0 weight percent sodium salicylic acid solution 3-Erucylamidopropyltrimethyl ammonium chloride (11.1 g of a 69.53 weight percent solution in isopropanol), prepared as in Example 2, is blended with 1,2-propanediol (1.90 g). The resulting product is then blended with water (80.6 g). Sodium salt of salicylic acid (3.7 grams, 30 weight percent) is added and the contents are blended. Additional water (12.7 g) is added and the contents are blended to give the title composition as a viscous solution.

EXAMPLE 12

The viscosity of compositions of Examples 10 and 11 is measured between 85° F. and 275° F. with a Fann 50 Rheometer equipped with a R1-B5 spindle setting at a shear rate of 118 rpm. The results are shown in Table 3. A viscosity of 100 cps at a shear rate of 100 sec$^{-1}$ is preferred to fracture the formation and carry proppant.

TABLE 3

Viscosity of Representative Salicylate Salt Compositions

| Example 10 0.623 wt. % Na Salicylic Acid | | Example 11 1.0 wt. % Na Salicylic Acid | |
|---|---|---|---|
| Temperature (° F.) | Viscosity (cps) | Temperature (° F.) | Viscosity (cps) |
| 200 | 5 | 220 | 4 |
| 194 | 7 | 212 | 8 |
| 185 | 15 | 203 | 15 |
| 176 | 40 | 194 | 31 |
| 166 | 90 | 184 | 74 |
| 156 | 129 | 175 | 181 |
| 145 | 151 | 165 | 324 |
| 134 | 131 | 156 | 359 |
| 125 | 118 | 146 | 304 |
| 116 | 109 | 136 | 237 |
| 105 | 136 | 127 | 212 |
| 90 | 146 | 119 | 259 |
| 77 | 161 | 110 | 279 |
| 73 | 161 | 101 | 389 |
| 73 | 168 | 93 | 421 |
| 73 | 187 | 88 | 490 |
| | | 84 | 1179 |
| | | 84 | 1316 |

As shown in Table 3, the compositions of Examples 10 and 11 provide more than 100 cps of viscosity at 156° and 175° F., respectively.

EXAMPLE 13

Preparation of 3-oleylamidopropyl dimethylamine

3-Oleylamidopropyl dimethylamine is prepared by heating oleic acid (818 g, 2.90 moles, Iodine value=199–204) with 3-(dimethylamino)propylamine (300 g, 2.94 moles) in a 2-liter high pressure vessel at a temperature up to 140° C. for 31 hours.

EXAMPLE 14

Preparation of 3-oleylamidopropyl trimethyl ammonium chloride

A mixture of 3-oleylamidopropyl dimethylamine (655 g), prepared as in Example 13, methyl chloride (104 g, 2.05 moles) and isopropanol (253 g) is heated in a 2-liter pressure vessel at a temperature up to 95° C. for 24 hours. Ethylene oxide (7 g) is added to the reaction product. Fifteen hours later, the pressure stabilizes and an additional 5 g (0.10 moles) of methyl chloride is added to quaternize the remaining amine. A chloride titration indicates that the resulting transparent amber colored liquid material is 73.99% active.

EXAMPLE 15

Preparation of an aqueous 4.04 weight percent 3-oleylamidopropyl trimethyl ammonium chloride, 1.42 weight percent isopropanol, 8.09 weight percent KCl solution 3-Oleylamidopropyl trimethyl ammonium chloride (6.0 g of a 73.99 weight percent solution in isopropanol), prepared as in from Example 14, is blended with water (83.5 g). Potassium chloride (8.9 g) is added and the contents are blended. Additional water (11.6 g) is added and contents are blended to give the title composition as a viscous solution in water.

EXAMPLE 16

Preparation of an aqueous 4.04 weight percent 3-oleylamidopropyl trimethyl ammonium chloride, 1.42 weight percent isopropanol, 10 weight percent KCl solution 3-Oleylamidopropyl trimethyl ammonium chloride (6.0 g of a 73.99 weight percent solution in isopropanol), prepared as in Example 14, is blended with water (82.3 g). Potassium chloride (11.0 g) is added and the contents are blended. Additional water (10.7 g) is added and contents are blended to give the title composition as a viscous solution in water.

EXAMPLE 17

The viscosity of compositions of Examples 15 and 16 is measured between 193° F. and 86° F. with a Brookfield Model DV-III Programmable Rheometer equipped with a SC4-34 spindle at a shear rate of 0.56 sec$^{-1}$. The results are shown in Table 4.

TABLE 4

Viscosity of Representative KCl Salt Compositions

| Temperature (° F.) | Example 15 8.09 wt. % KCl Viscosity (cps) | Temperature (° F.) | Example 16 10 wt. % KCl Viscosity (cps) |
|---|---|---|---|
| 193 | 30 | 193 | 150 |
| 190 | 30 | 190 | 150 |
| 185 | 60 | 185 | 120 |
| 179 | 60 | 179 | 120 |
| 175 | 120 | 175 | 150 |
| 170 | 150 | 170 | 150 |
| 166 | 150 | 166 | 180 |
| 160 | 180 | 160 | 270 |
| 155 | 180 | 155 | 300 |
| 150 | 180 | 150 | 450 |
| 146 | 210 | 146 | 510 |
| 141 | 240 | 141 | 690 |
| 136 | 300 | 135 | 990 |
| 131 | 360 | 131 | 1380 |
| 126 | 420 | 126 | 1680 |
| 121 | 510 | 121 | 2280 |
| 115 | 690 | 116 | 2969 |
| 110 | 780 | 110 | 4289 |
| 105 | 1050 | 105 | 5999 |
| 101 | 1500 | 101 | 8428 |
| 95 | 2429 | 95 | 13077 |
| 91 | 3479 | 90 | 18086 |
| 86 | 6989 | 86 | 29334 |

As shown in Table 4, the compositions of Examples 15 and 16 provide more than 100 cps of viscosity at 175° F. and 193° F.

EXAMPLE 18

Preparation of 3-Erucylamidopropyl bis(ethyl)amine

Erucic acid (871 g, 2.57 moles, Iodine value=74–78) is reacted with 3(diethylamino)propylamine (335 g, 2.57 moles) in a 2-liter high pressure vessel at a temperature up to 150° C. for 26 hours to give 3-erucylamidopropyl diethylamine.

EXAMPLE 19

Preparation of 3-Erucylamidopropyl bis(ethyl)methyl ammonium chloride

3-Erucylamidopropyl diethylamine (724 g), methyl chloride (85 g, 1.68 moles) and isopropanol (269 g) are heated in a 2-liter pressure vessel at a temperature up to 100° C. for 7 hours. Ethylene oxide (11 g, 0.25 moles) is added to the reaction product. After 20 hours, the pressure stabilizes and an additional 13 g (0.26 moles) of methyl chloride is added to quaternize the remaining amine. A chloride titration indicates that the product is 84.09% active. The product is an opaque cream colored liquid at room temperature.

COMPARATIVE EXAMPLE 20

Preparation of 3-erucylamidopropyl(dimethyl)amine

The title compound is prepared by heating a mixture of erucic acid (854 g, 2.52 moles, Iodine value=74–78) and 3-(dimethylamino)propylamine (261 g, 2.55 moles) is heated in a 2 liter high pressure vessel at a temperature up to 150° C. for 26 hours to give the title compound.

COMPARATIVE EXAMPLE 21

Preparation of 3-erucylamidopropyltrimethyl ammonium chloride without ethylene oxide A mixture of 3-erucylamidopropyltrimethyl ammonium chloride (684 g), prepared as in Example 21, methyl chloride (81 g, 1.84 moles) and isopropanol (255 g) are reacted in a 2 liter pressure vessel at a temperature up to 100° C. for 22 hours. A chloride titration of the product indicates that the material is 73.82% active. The product is a transparent amber colored liquid at room temperature.

COMPARATIVE EXAMPLE 22

Preparation of a 62.75 weight percent 3-erucylamidopropyltrimethylammonium chloride, 22.25 weight percent isopropanol, 10 weight percent 1,2-propanediol, 5% water solution The title composition is prepared by blending 3-Erucylamidopropyltrimethylammonium chloride (255.0 g, 73.82 weight percent solution in isopropanol), prepared as in Example 21 without ethylene oxide, with 1,2-propanediol (10 g) and water (15 g).

COMPARATIVE EXAMPLE 23

Preparation of an aqueous 3.99 weight percent 3-erucylamidopropyltrimethyl ammonium chloride (without ethylene oxide), 1.42 weight percent isopropanol, 0.636 weight percent 1,2-propanediol, 5.0 weight percent $NH_4$ Cl solution The 3-Erucylamidopropyltrimethylammonium chloride solution in isopropanol, water and 1,2-propanedil solution of Comparative Example 22 (14 g), is blended in a Waring blender with water (184.7 g). Ammonium chloride (11.0 g) is added and the contents are blended. Additional water (10.3 g) is added and the contents are blended to give the title composition as a viscous liquid.

EXAMPLE 24

Preparation of 59.08 weight percent 3-erucylamidopropyltrimethylammonium chloride, 25.92 weight percent isopropanol, 10 weight percent 1,2-propanediol, 5 weight percent water solution 3-Erucylamidopropyltrimethylammonium chloride (170.0 g, 69.5 weight percent solution in 30.5 isopropanol), prepared using ethylene oxide as in Example 2, is blended with 1,2-propanediol (20 g) and water (10 g). The freezing point of this formulation is −3° F.

EXAMPLE 25

Preparation of an aqueous 3.99 weight percent 3-erucylamidopropyltrimethyl ammonium chloride (with ethylene oxide), 1.75 weight percent isopropanol, 0.68 weight percent 1,2-propanediol, 5.0 weight percent $NH_4Cl$ solution The 3-erucylamidopropyltrimethylammonium chloride solution in water, isopropanol and 1,2-propanediol of Example 24 (14.9 g) is blended in a Waring blender with water (180.5 g). Ammonium chloride (11.0 g) is added and the contents are blended. Additional water (13.7 g) is added and the contents are blended to give the title composition as a viscous liquid.

EXAMPLE 26

The viscosity of the compositions of Comparative Example 23 and Example 25 are determined between 85° F. and 260° F. with a Farm 50 Rheometer equipped with a R1-B5 spindle setting at a shear rate of 118 rpm. The results are shown in Table 5. A viscosity of 100 cps at a shear rate of 100 $sec^{-1}$ is preferred to fracture the formation and carry proppant.

TABLE 5

Viscosity of Representative $NH_4Cl$ Salt Compositions

| Temperature (° F.) | Example 23 without ethylene oxide Viscosity (cps) | Temperature (° F.) | Example 25 with ethylene oxide Viscosity (cps) |
|---|---|---|---|
| 265 | 30 | 265 | 54 |
| 260 | 32 | 260 | 62 |
| 256 | 42 | 259 | 66 |
| 246 | 53 | 257 | 72 |
| 240 | 81 | 253 | 121 |
| 235 | 111 | 246 | 87 |
| 228 | 145 | 239 | 163 |
| 215 | 182 | 228 | 209 |
| 175 | 191 | 210 | 211 |
| 100 | 185 | 163 | 149 |
| 80 | 245 | 107 | 103 |
|  |  | 76 | 176 |

As shown in Table 5, the composition of Example 25 provides more than 100 cps of viscosity at 246° while the composition of Comparative Example 23 provides more than 100 cps of viscosity at 235° F. The composition of Example 25 is prepared using ethylene oxide and Comparative Example 23 is prepared without ethylene oxide. Therefore, the composition prepared with ethylene oxide (Example 25) can be used to fracture hotter wells than the composition prepared without ethylene oxide (Comparative Example 23).

Although this invention has been described in detail for the purpose of illustration, it is to be understood that such detail is solely for that purpose and that numerous modifications, alterations and changes can be made therein by those skilled in the art without departing from the spirit and scope of the invention except as it may be limited by the claims. All changes which come within the meaning and range of equivalency of the claims are to be embraced within their scope.

What is claimed is:

1. A method of preparing a quaternized amidoamine surfactant of formula

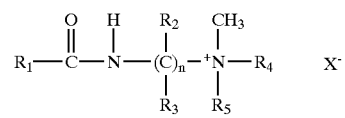

wherein
  $R_1$ is selected from the group consisting of $C_{12}$–$C_{30}$ alkyl, $C_{12}$–$C_{30}$ alkenyl, $C_{12}$–$C_{30}$ arylalkyl and $C_{12}$–$C_{30}$ cycloalkylalkyl,
  $R_2$ and $R_3$ are independently selected at each occurrence from hydrogen or $C_1$–$C_4$ alkyl,
  $R_4$ and $R_5$ are independently selected from $C_1$–$C_4$ alkyl, $C_1$–$C_4$ alkoxyalkyl and $C_1$–$C_4$ hydroxyalkyl, X is halide; and n is an integer from 1 to about 10 comprising reacting an amidotertiaryamine of formula $$R_1-\overset{O}{\underset{}{C}}-\overset{H}{\underset{}{N}}-(\overset{R_2}{\underset{R_3}{C}})_n-N\overset{R_4}{\underset{R_5}{\diagdown}}$$

with methyl halide and alkylene oxide.

2. The method of claim 1 wherein the methyl halide is added prior to the alkylene oxide.

3. The method of claim 2 wherein additional methyl halide is added subsequently to the alkylene oxide.

4. The method of claim 1 wherein the alkylene oxide is ethylene oxide.

5. The method of claim 1 wherein the reaction is carried out in a $C_1$–$C_4$ alcohol.

6. The method of claim 5 wherein the alcohol is isopropanol.

7. The method of claim 1 wherein $R_1$ is selected from the group consisting of $C_{12}$–$C_{30}$ alkyl and $C_{12}$–$C_{30}$ alkenyl.

8. The method of claim 1 wherein $R_1$ is $C_{12}$–$C_{30}$ alkenyl.

9. The method of claim 1 wherein $R_1$ is $C_{18}$–$C_{30}$ alkenyl.

10. The method of claim 1 wherein $R_1$ is $C_{18}$–$C_{30}$ alkenyl; $R_2$ and $R_3$ are hydrogen; $R_4$ and $R_5$ are independently selected from $C_1$–$C_2$ alkyl and $C_1$–$C_2$ hydroxyalkyl; and n is an integer of 2 to about 6.

11. The method of claim 10 wherein $R_4$ and $R_5$ are methyl.

12. A quaternized amidoamine surfactant prepared according to the method of claim 1.

13. A quaternized amidoamine surfactant composition comprising about 40 to about 80 weight percent of the quaternized amidoamine surfactant of claim 12 and about 20 to about 60 weight percent of one or more $C_1$–$C_4$ alcohols.

14. The quaternized amidoamine surfactant composition of claim 13 wherein the $C_1$–$C_4$ alcohol is isopropanol.

15. An aqueous composition comprising
a) about 75 to about 90 weight percent of the quaternized amidoamine surfactant composition of claim 12;
b) about 1 to about 15 weight percent of one or more $C_2$–$C_4$ diols; and
c) about 1 to about 10 weight percent water.

16. The aqueous composition of claim 15 wherein the $C_2$–$C_6$ diol is 1,2-propane diol.

17. The aqueous composition of claim 15 that has a pour point of less than 40° F.

18. A gelled aqueous composition comprising
a) about 0.5 to about 10 weight percent of the aqueous composition of 15;
b) about 0.5 to about 10 weight percent of one or more salts or one or more $C_4$–$C_{10}$ alcohols; and
c) water.

19. The gelled aqueous composition of claim 18 wherein the salts are selected from potassium chloride, ammonium chloride, sodium salicylate and mixtures thereof.

20. The gelled aqueous composition of claim 18 wherein the $C_4$–$C_{10}$ alcohol is selected from the group consisting of hexanol, octanol and decanol.

21. The gelled aqueous composition of claim 18 further comprising about 0.5 to about 8 pounds per gallon of a particulate proppant suspended therein.

22. A method of treating a well in a subterranean formation comprising pumping into the well the gelled aqueous composition of claim 18.

23. The method of claim 22 wherein the treating is selected from drilling, hydraulic fracturing, gravel placement, scale removing and mud cake removing operations.

24. A method of fracturing a subterranean formation comprising pumping into the formation at a pressure sufficient to fracture the formation the gelled aqueous composition of claim 21.

* * * * *